(12) United States Patent
Li et al.

(10) Patent No.: US 12,168,813 B2
(45) Date of Patent: Dec. 17, 2024

(54) ELECTROKINETIC DEVICE AND METHOD FOR IN-SITU LEACHING OF URANIUM

(71) Applicant: UNIVERSITY OF SOUTH CHINA, Hengyang (CN)

(72) Inventors: Chunguang Li, Hengyang (CN); Longcheng Liu, Hengyang (CN); Chong Zhang, Hengyang (CN); Kaixuan Tan, Hengyang (CN); Zhenzhong Liu, Hengyang (CN); Yongmei Li, Hengyang (CN); Shuo Meng, Hengyang (CN); Wenji Wang, Hengyang (CN); Qi Liu, Hengyang (CN); Qianjin Niu, Hengyang (CN)

(73) Assignee: UNIVERSITY OF SOUTH CHINA (CN)

( * ) Notice: Subject to any disclaimer, the term of this patent is extended or adjusted under 35 U.S.C. 154(b) by 0 days.

(21) Appl. No.: 18/134,161

(22) Filed: Apr. 13, 2023

(65) Prior Publication Data

US 2024/0117467 A1    Apr. 11, 2024

(30) Foreign Application Priority Data

Apr. 13, 2022   (CN) .......................... 202210386868.4

(51) Int. Cl.
*E21B 43/28* (2006.01)
*C22B 3/02* (2006.01)
(Continued)

(52) U.S. Cl.
CPC ............ *C22B 60/0221* (2013.01); *C22B 3/02* (2013.01); *C22B 3/045* (2013.01); *E21B 43/28* (2013.01);
(Continued)

(58) Field of Classification Search
CPC ....... C22B 3/02; C22B 3/045; C22B 60/0221; E21B 43/08; E21B 43/28; E21B 47/00;
(Continued)

(56) References Cited

U.S. PATENT DOCUMENTS

| 3,713,698 | A | * | 1/1973 | Rhoades | ................ E21B 43/28 |
| | | | | | 423/20 |
| 4,071,278 | A | * | 1/1978 | Carpenter | ........... E21B 43/2405 |
| | | | | | 205/49 |

(Continued)

FOREIGN PATENT DOCUMENTS

| CN | 106507866 | | 7/2014 |
| CN | 113651397 | A * | 11/2021 |

OTHER PUBLICATIONS

Chinese Office Action dated Oct. 17, 2022 issued in corresponding Chinese Application No. 202210386868.4, with machine translation to English.

*Primary Examiner* — Daniel P Stephenson
(74) *Attorney, Agent, or Firm* — Onello & Mello, LLP (57) ABSTRACT

Provided are an electrokinetic device and method for in-situ leaching of uranium. The electrokinetic device for in-situ leaching of uranium includes an injection well, a pumping well, a positive electrode, a negative electrode, leaching solution, and a direct current power supply. Uranium ore is provided between the injection well and the pumping well, the negative electrode is arranged in the injection well, and the positive electrode is arranged in the pumping well. The leaching solution is injected from the injection well, flows through the uranium ore, and then is pumped from the pumping well for uranium extraction. The direct current power supply is respectively connected to the positive electrode and the negative electrode, and is configured to apply direct current between the positive electrode and the (Continued)

negative electrode to promote the pooling of uranium-carrying ions towards the pumping well.

6 Claims, 8 Drawing Sheets

(51) Int. Cl.
    *C22B 3/04* (2006.01)
    *C22B 60/02* (2006.01)
    *E21B 43/08* (2006.01)
    *E21B 47/00* (2012.01)
    *G01N 33/18* (2006.01)
    *G01N 33/20* (2019.01)

(52) U.S. Cl.
    CPC .............. *E21B 47/00* (2013.01); *E21B 43/08* (2013.01); *G01N 33/18* (2013.01); *G01N 33/20* (2013.01)

(58) Field of Classification Search
    CPC ........ E21B 43/00; G01N 33/18; G01N 33/20; Y02P 10/20
    See application file for complete search history.

(56) References Cited

U.S. PATENT DOCUMENTS

| | | | |
|---|---|---|---|
| 4,206,024 A * | 6/1980 | Carpenter | E21B 43/17 |
| | | | 205/766 |
| 5,458,747 A * | 10/1995 | Marks | B09C 1/085 |
| | | | 205/702 |
| 8,926,814 B2 | 1/2015 | He et al. | |
| 2011/0024361 A1* | 2/2011 | Schwartzel | C02F 1/467 |
| | | | 204/290.01 |
| 2014/0339086 A1 | 11/2014 | He et al. | |
| 2016/0045841 A1* | 2/2016 | Kaplan | C01B 32/05 |
| | | | 429/49 |
| 2024/0117467 A1* | 4/2024 | Li | E21B 43/28 |

* cited by examiner

ELECTROKINETIC DEVICE AND METHOD FOR IN-SITU LEACHING OF URANIUM

CROSS-REFERENCE TO RELATED APPLICATION

This patent application claims the benefit and priority of Chinese Patent Application No. 202210386868.4, filed with the China National Intellectual Property Administration on Apr. 13, 2022, the disclosure of which is incorporated by reference herein in its entirety as part of the present application.

TECHNICAL FIELD

The present disclosure relates to the field of in-situ leaching of uranium, and in particular to an electrokinetic device and method for in-situ leaching of uranium.

BACKGROUND

Uranium is an important nuclear fuel and national defense strategic resource, which is mainly mined by in-situ leaching at present. However, whether in-situ leaching technology can be applied to uranium reservoirs depends on porosity and permeability. When the permeability is less than 0.1 m/d, it is still impossible to achieve economic exploitation through in-situ leaching. For uranium ore with permeability greater than or equal to 0.1 m/d, the in-situ leaching technology can be used for mining, but from the start of production, it is necessary to keep continuous pumping and injection to maintain cone of depression to minimize the impact on the ambient environment, which leads to high energy consumption and is not conducive to the realization of the policy target of double carbon.

At a global level, the development of in-situ leaching of uranium has mainly experienced three stages, i.e., acid leaching, alkali leaching and neutral ($CO_2+O_2$) leaching technologies, but two bottlenecks of low-permeability uranium deposit mining and long production cycle have not been completely solved. For the problem of low permeability, the researchers have discussed physical methods such as in-situ blasting and hydraulic fracturing, and permeability enhancement of application of chemical methods such as surfactants and inorganic acids through theory and experiments, but the physical methods are difficult to implement on site and the chemical methods have limited permeability enhancement ability. Moreover, as preferential flows generally exist during in-situ leaching of uranium, the leaching agent can only flow through a small part of orebodies, resulting in long uranium mining cycle and low efficiency.

Based on above problems, a new uranium mining method is urgently needed to improve the permeability and leaching effect of conventional permeable sandstones.

SUMMARY

An objective of the present disclosure is to provide an electrokinetic device and method for in-situ leaching of uranium, which can improve the uranium mining efficiency of conventional permeable sandstones.

To achieve the objective above, the present disclosure provides the following solutions:

An electrokinetic device for in-situ leaching of uranium includes: an injection well, a pumping well, a positive electrode, a negative electrode, leaching solution, and a direct current power supply.

Uranium ore is provided between the injection well and the pumping well.

The negative electrode is arranged in the injection well.

The positive electrode is arranged in the pumping well.

The leaching solution is injected from the injection well, flows through the uranium ore, and then is pumped from the pumping well for uranium extraction.

The direct current power supply is respectively connected to the positive electrode and the negative electrode, and is configured to apply direct current between the positive electrode and the negative electrode to promote the pooling of uranium-carrying ions towards the pumping well.

Alternatively, the positive electrode and the negative electrode are both electrode bars.

Alternatively, the injection well includes a cathode chamber, an injection chamber, and an anion exchange membrane. The pumping well includes an anode chamber, a pumping chamber, and a cation exchange membrane.

The anion exchange membrane is provided between the cathode chamber and the injection chamber, and the cation exchange membrane is provided between the anode chamber and the pumping chamber.

The negative electrode is arranged in the cathode chamber, and the positive electrode is arranged in the anode chamber.

The uranium ore is provided between the injection chamber and the pumping chamber.

The leaching solution is injected from the injection chamber, flows through the uranium ore, and then is pumped from the pumping chamber.

Alternatively, the cathode chamber and the anode chamber each are filled with electrode protection solution.

Alternatively, the electrokinetic device for in-situ leaching of uranium further includes:

a first connector, respectively connected to the positive electrode and the cation exchange membrane and configured to fix the positive electrode to the cation exchange membrane; and a second connector, respectively connected to the negative electrode and the anion exchange membrane and configured to fix the negative electrode to the anion exchange membrane.

Alternatively, the electrokinetic device for in-situ leaching of uranium further includes:

a first filter, arranged in the injection well and attached to a well wall of the injection well; and a second filter, arranged in the pumping well and attached to a well wall of the pumping well.

Alternatively, the injection well and the pumping well are both located in an underground uranium-containing stratum.

The electrokinetic device for in-situ leaching of uranium further includes:

a first casing, extending from the ground to a top surface of the injection well; and a second casing, extending from the ground to a top surface of the pumping well.

Alternatively, the electrokinetic device for in-situ leaching of uranium further includes:

a first voltage-current monitoring component, arranged in the injection well and configured to detect a voltage and current in the injection well; and a second voltage-current monitoring component, arranged in the pumping well and configured to detect a voltage and current in the pumping well.

To achieve the objective, the present disclosure further provides the following solutions:

An electrokinetic method for in-situ leaching of uranium applying the electrokinetic device for in-situ leaching of uranium includes the following steps:

carrying out geological exploration and geophysical exploration in a to-be-mined area to determine uranium orebody morphology in the to-be-mined area, and analyzing a core sample of a uranium orebody to determine physical and chemical parameters of the core sample;

determining initial mine shaft parameters according to the uranium orebody morphology and the physical and chemical parameters of the core sample, where the initial mine shaft parameters include well types, well diameters and well spacing of a pumping well and an injection well;

determining initial leaching solution parameters by a horizontal column leaching test, where the initial leaching solution parameters include types, concentrations and liquid-solid ratios of an oxidant and a leaching agent;

carrying out a laboratory test according to the initial mine shaft parameters, the initial leaching solution parameters and the core sample of the uranium orebody and based on the electrokinetic device for in-situ leaching of uranium, applying direct currents with different potential gradients between a positive electrode and a negative electrode, and determining an optimal potential gradient according to a uranium concentration in pumped leaching solution, where uranium ore in the electrokinetic device for in-situ leaching of uranium is the core sample of the uranium ore body;

based on the optimal potential gradient, changing the types, concentrations and potential gradients of the oxidant and the leaching solution by an orthogonal experiment to determine optimal leaching solution parameters;

manufacturing a simulated miniature uranium mine according to the physical and chemical parameters of the core sample; according to the optimal potential gradient and the optimal leaching solution parameters and based on the electrokinetic device for in-situ leaching of uranium, applying the positive electrode and the negative electrode to the simulated miniature uranium mine, carrying out a scale-up experiment to optimize the initial mine shaft parameters to obtain optimized mine shaft parameters, where the uranium ore in the electrokinetic device for in-situ leaching of uranium is the simulated miniature uranium mine;

according to the optimized mine shaft parameters, the optimal leaching solution parameters and the optimal potential gradient and based on the electrokinetic device for in-situ leaching of uranium, carrying out a field condition test in the to-be-mined area to determine field semi-quantitative parameters;

optimizing the optimized mine shaft parameters according to the field-semi-quantitative parameters to obtain final mine shaft parameters; and based on the final mine shaft parameters, the optimal leaching solution parameters and the optimal potential gradient, arranging the electrokinetic device for in-situ leaching of uranium at the position of an underground uranium-containing stratum in the to-be-mined area for uranium mining.

Alternatively, the electrokinetic method for in-situ leaching of uranium further includes the following steps:

collecting a water sample from a uranium-containing stratum in the to-be-mined area in real time, and analyzing the water sample to determine water sample parameters; and determining the influence of a uranium mining process on ambient environment according to the physical and chemical parameters of the core sample and the water sample parameters.

According to specific embodiments provided by the present disclosure, the present disclosure has the following technical effects: a negative electrode is arranged in an injection well and a positive electrode is arranged in a pumping well. Leaching solution is injected from the injection well, flows through the uranium ore, and then is pumped from the pumping well. By applying direct current between the positive electrode and the negative electrode, an electric field is used to promote the pooling of uranium-carrying ions towards the pumping well, and thus the probability of chemical clogging is reduced, the migration of pollutants to the ambient environment is limited, the permeability and porosity of uranium ore are improved, and the uranium mining efficiency of conventional permeable sandstone is improved.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

In the drawings.

1—injection well, 101—cathode chamber, 102—anion exchange membrane, 103—injection chamber, 104—electrode protection solution adding port, 105—injection hole, 2—pumping well, 201—anode chamber, 202—cation exchange membrane, 203—pumping chamber, 205—pumping hole, 3—negative electrode, 4—positive electrode, 5—uranium ore, 6—direct current power supply, 7—wire, 8—first casing, 9—second casing, 10—first filter, 11—second filter, 12—first connector, 13—second connector, 14—universal meter.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

An objective of the present disclosure is to provide an electrokinetic device and method for in-situ leaching of uranium. By arranging a negative electrode in an injection well and a positive electrode in a pumping well, an electric field is used to promote the pooling of uranium-carrying ions towards the pumping well, and thus the probability of chemical clogging is reduced, the migration of pollutants to the ambient environment is limited, the permeability and porosity of uranium ore are improved, and the uranium mining efficiency of conventional permeable sandstone is improved.

To make the objectives, features and advantages of the present disclosure more apparently and understandably, the following further describes the present disclosure in detail with reference to the accompanying drawings and the specific embodiments.

Figure 1:
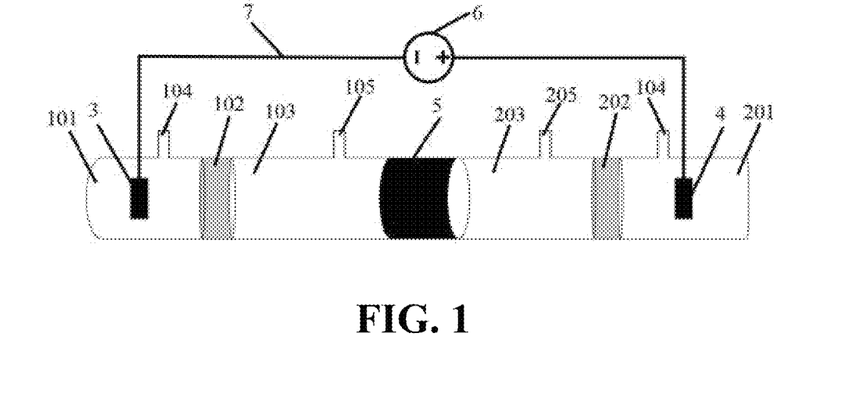
FIG. 1 is a structure schematic diagram of a horizontal column leaching test device.
Figure 2:
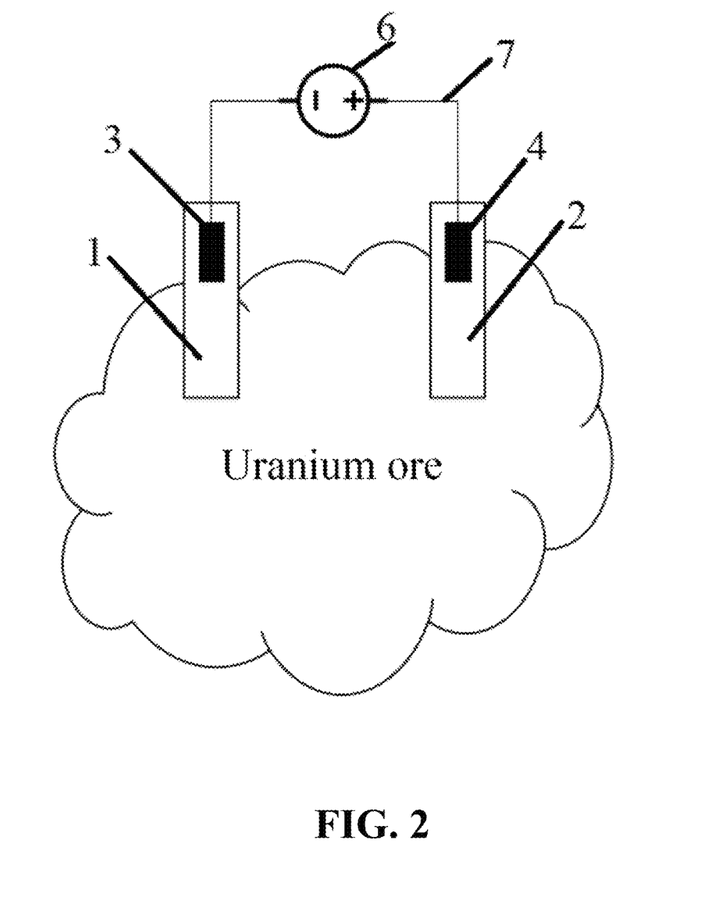
FIG. 2 is a structure schematic diagram of a miniature uranium mine test device.
Figure 3:
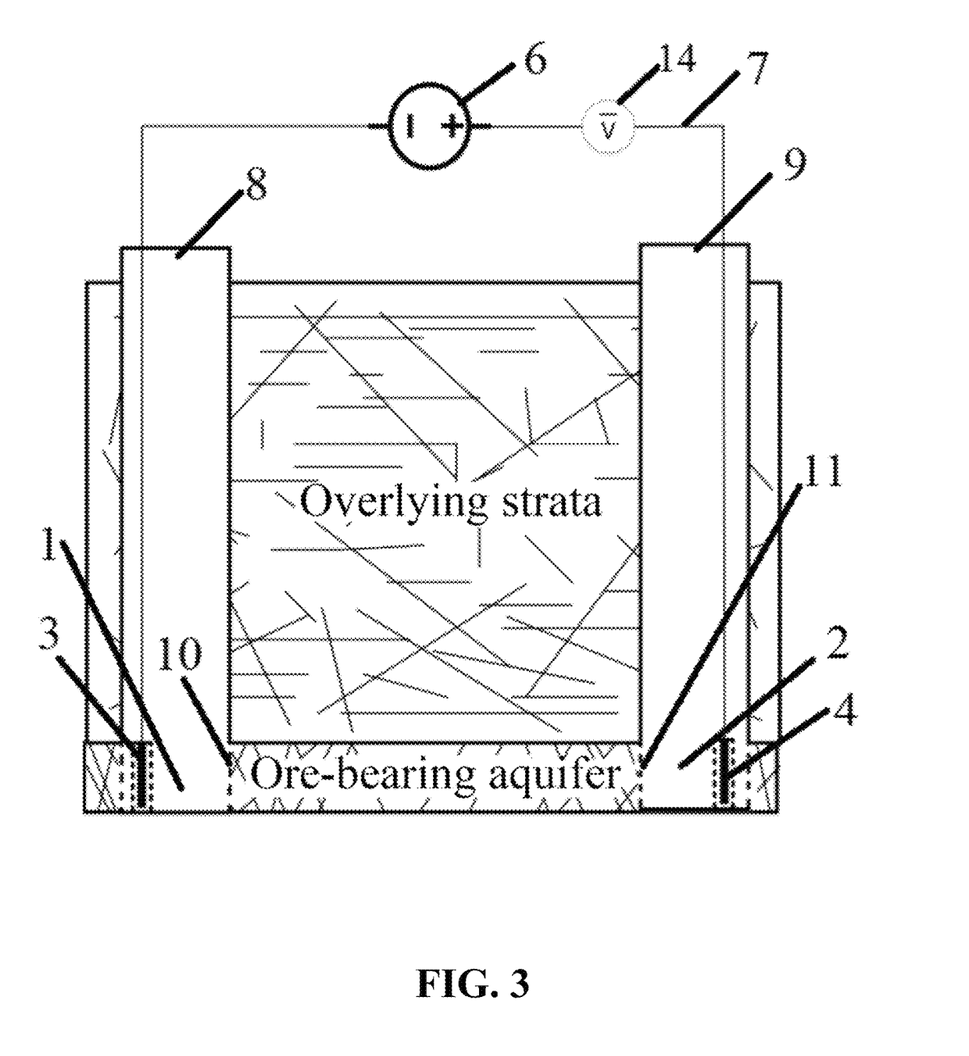
FIG. 3 is a schematic diagram of the application of an electrokinetic device for in-situ leaching of uranium in accordance with the present disclosure to in-situ uranium mining.

As shown in FIG. 1 through FIG. 3, an electrokinetic device for in-situ leaching of uranium includes an injection well 1, a pumping well 2, a positive electrode 4, a negative electrode 3, leaching solution, and a direct current power supply 6.

Uranium ore 5 is provided between the injection well 1 and the pumping well 2.

The negative electrode 3 is arranged in the injection well 1, and the positive electrode 4 is arranged in the pumping well 2. Preferably, the positive electrode 4 and the negative electrode 3 are both electrode bars. The positive electrode 4 and the negative electrode 3 are both connected to the direct current power supply 6 by wires 7.

The leaching solution is injected from the injection well 1, flows through the uranium ore 5 and then is pumped from the pumping well 2 for uranium extraction.

The direct current power supply 6 is respectively connected to the positive electrode 4 and the negative electrode 3. The direct current power supply 6 is configured to apply direct current between the positive electrode 4 and the negative electrode 3 to promote the pooling uranium-carrying ions towards the pumping well 2.

Further, the injection well 1 includes a cathode chamber 101, an injection chamber 103, and an anion exchange membrane 102. The pumping well 2 includes an anode chamber 201, a pumping chamber 203, and a cation exchange membrane 202.

The anion exchange membrane 102 is provided between the cathode chamber 101 and the injection chamber 103, and the cation exchange membrane 202 is provided between the anode chamber 201 and the pumping chamber 203.

The negative electrode 3 is arranged in the cathode chamber 101, and the positive electrode 4 is arranged in the anode chamber 201. Preferably, the cathode chamber 101 and the anode chamber 201 are both filled with electrode protection solution.

The uranium ore 5 is provided between the injection chamber 103 and the pumping chamber 203.

The leaching solution is injected from the injection chamber 103, flows through the uranium ore 5, and then is pumped from the pumping chamber 203.

The injection well 1 is divided into the injection chamber 103 and the cathode chamber 101 by the anion exchange membrane 102. The pumping well 2 is divided into the pumping chamber 203 and the cathode chamber 201 by the cation exchange membrane 202. The purpose of division is to ensure that uranium-carrying ions can be pooled towards the pumping chamber 203 under the coupling effect of hydraulic power and electromigration and are prevented from penetrating through the cation exchange membrane 202 to be deposited in the cathode chamber 101, and to ensure that cations cannot penetrate through the anion exchange membrane 102 to reach the cathode chamber 101 while being pooled towards the injection chamber 103, thereby avoiding excessive depletion of the negative electrode 3.

In addition, the electrokinetic device for in-situ leaching of uranium further includes a first connector 12 and a second connector 13.

The first connector 12 is respectively connected to the positive electrode 4 and the cation exchange membrane 202, and is configured to fix the positive electrode 4 to the cation exchange membrane 202.

The second connector 13 is respectively connected to the negative electrode 3 and the anion exchange membrane 102, and is configured to fix the negative electrode 3 to the anion exchange membrane 102.

Further, the electrokinetic device for in-situ leaching of uranium further includes anion exchange membrane clamping plates and cation exchange membrane clamping plates. The anion exchange membrane 102 is fixed by the anion exchange membrane clamping plates, and the cation exchange membrane is fixed by the cation exchange membrane clamping plates.

The electrokinetic device for in-situ leaching of uranium further includes a third connector and a fourth connector. The third connector is respectively connected to the cation exchange membrane 202 and a first casing 8, and is configured to fix the cation exchange membrane 202 into the first casing 8. The fourth connector is respectively connected to the anion exchange membrane 102 and a second casing 9, and is configured to fix the anion exchange membrane 102 into the second casing 9.

In this embodiment, the electrode bars are connected to the ion exchange membrane clamps by the connectors and are fixed to the ion exchange membrane clamping plates, and the ion exchange membrane clamping plates are connected to the casings by the connectors.

In order to avoid the influence of uranium mining process on the ambient environment, the electrokinetic device for in-situ leaching of uranium further includes a first filter 10 and a second filter 11. The first filter 10 is arranged in the injection well 1 and is attached to a well wall of the injection well 1. The second filter 11 is arranged in the pumping well 2 and is attached to a well wall of the pumping well 2.

Figure 4:
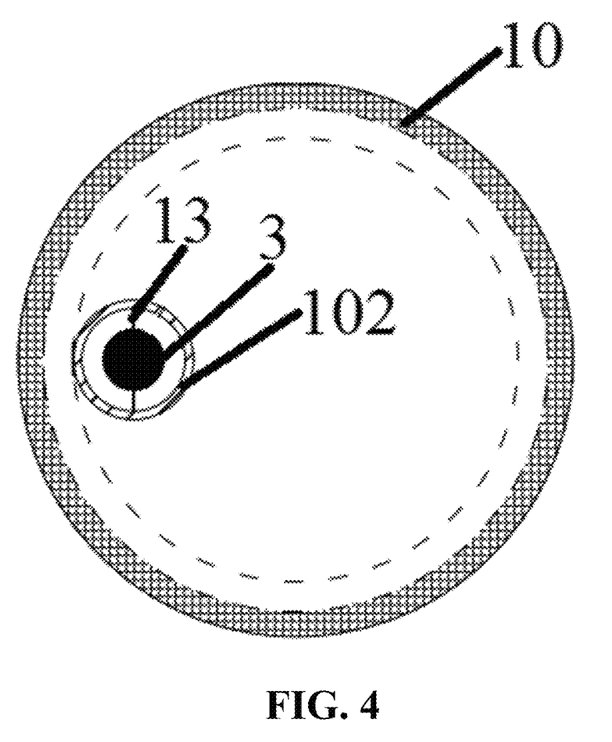
FIG. 4 is a profile of an injection well.
Figure 5:
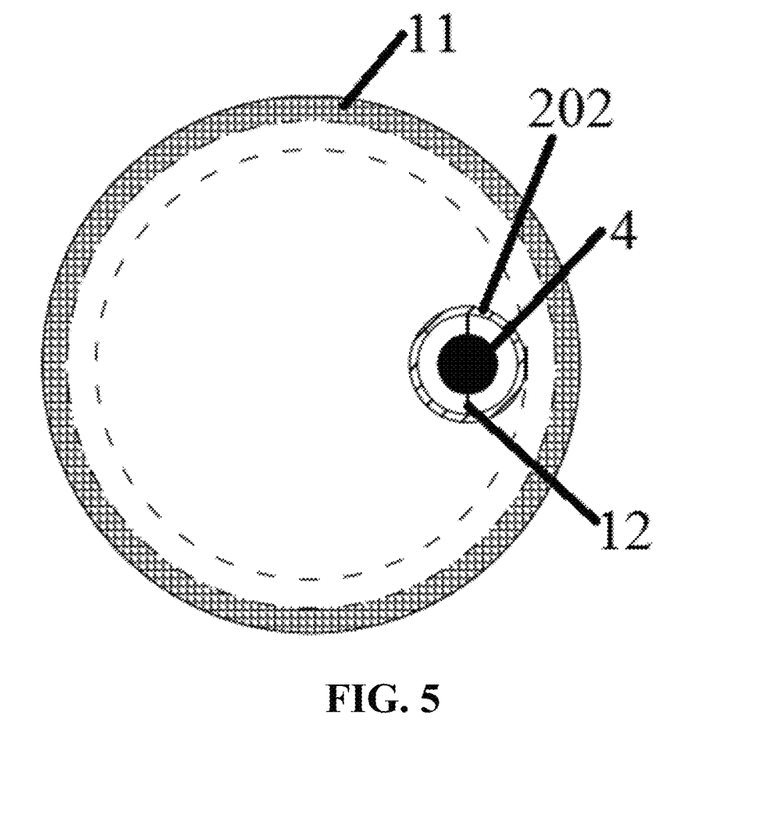
FIG. 5 is a profile of a pumping well.

Further, during in-situ mining, the injection well 1 and the pumping well 2 are both located in an underground uranium-containing stratum. The electrokinetic device for in-situ leaching of uranium further includes a first casing 8 and a second casing 9. The first casing 8 extends from the ground to a top face of the injection well 1. The second casing 9 extends from the ground to a top face of the pumping well 2. Specifically, diameters of the first casing 8 and the second casing 9 can be adjusted according to actual conditions.

Still further, the electrokinetic device for in-situ leaching of uranium further includes a first voltage-current monitoring component and a second voltage-current monitoring component. The first voltage-current monitoring component is arranged in the injection well 1, and is configured to detect a voltage and current in the injection well 1. The second voltage-current monitoring component is arranged in the pumping well 2, and is configured to detect a voltage and current in the pumping well 2. Specifically, the voltage-current monitoring components are installed within a certain range below liquid levels of the injection well 1 and the pumping well 2, and vertical positions can be adjusted according to the specific amount of liquid pumping and injection.

Further, the electrokinetic device for in-situ leaching of uranium further includes a universal meter 14. The universal meter 14 is connected to the direct current power supply 6, and is configured to detect a voltage and current generated by the direct current power supply 6.

In recent years, electrochemical technology has developed rapidly, which can be used to separate metal ions from solution and has been widely used in the fields of metallurgy, chemical industry, environment and the like. An electric field can promote the migration of solute, and compared with single analytical diffusion, the electromigration rate of the solute is four times faster in clay and one hundred times faster in fractured crystalline salt. Based on the principle of electromigration acceleration, international researchers have experimentally combined numerical simulations to predict the time that nuclides penetrate into wall rocks of granite-type underground repositories, which turns the prediction of migration range for tens of thousands of years into reality. The electromigration rate of ions through intact crystalline rocks can be several orders of magnitude faster than molecular diffusion. The above facts have proved that the electric field has remarkable advantages in promoting nuclide migration. The electromigration rate depends on the curvature rather than the hydraulic conductivity, which can promote the leaching agent to be transported to the target metal more evenly, and is not limited to a specific preferential flow channel.

The application of in-situ leaching of uranium is limited to sedimentary rocks with sufficient hydraulic permeability, while the process of electrokinetic in-situ leaching does not only rely on hydraulic induction for solute migration, which can achieve almost uniform permeation in space by using the electric field as a driving force. Therefore, it is of a great scientific significance and application value to introduce an electrokinetic field into the in-situ leaching of uranium to study the method of electrokinetic in-situ leaching of uranium (EK-ISLU) and develop the EK-ISLU technology, it is expected to promote the innovation of the theory and technology of in-situ leaching of uranium, improve the scope of application and mining efficiency of in-situ leaching of uranium, reduce the pollution to the surrounding water bodies, improve the economy of uranium mining, ensure the supply of uranium resources in the nuclear industry and national defense, and help achieve the target of double carbon.

To understand the solution of the present disclosure more clearly, the present disclosure is further described below with reference to specific embodiments.

In an embodiment, a horizontal column leaching test device is constructed based on the electrokinetic device for in-situ leaching of uranium.

The horizontal column leaching test device is mainly used in laboratory tests. As shown in FIG. 1, the horizontal column leaching test device includes a cathode chamber 101, an anion exchange membrane 102, an injection chamber 103, uranium ore 5, a pumping chamber 203, a cation exchange membrane 202 and an anode chamber 201 in sequence in a horizontal direction.

In this embodiment, the cathode chamber 101 and the anode chamber 201 are both provided with electrode protection solution adding ports 104. The injection chamber 103 is provided with an injection hole 105, and a pumping chamber 203 is provided with a pumping hole 204. Leaching solution is injected from the injection hole 105, the leaching solution permeated by the uranium ore 5 is pumped through the pumping hole 204, so as to carry out a laboratory test with a uranium ore sample.

In an embodiment, a miniature uranium mine test device is constructed based on the electrokinetic device for in-situ leaching of uranium.

Uranium ore in the miniature uranium mine test device is manufactured according to physical and chemical parameters of a core sample by using an ore press. As shown in FIG. 2, in this embodiment, an injection well 1 and a pumping well 2 are embedded in the uranium ore. An injection chamber 103 is inside the injection well 1 and a pumping chamber 203 is inside the pumping well 2.

In this embodiment, in-situ uranium mining is carried out based on the electrokinetic device for in-situ leaching of uranium. As shown in FIG. 3 through FIG. 5, in this embodiment, both the injection well 1 and the pumping well 2 are located in an underground uranium-containing stratum. A first casing 8 extends from the ground to a top face of the injection well 1, and a second casing 9 extends from the ground to a top face of the pumping well 2. The injection chamber 103 is inside the injection well 1 and the pumping chamber 203 is inside the pumping well 2. The injection chamber 103 is isolated from a cathode chamber 101 by an anion exchange membrane 102, and the pumping chamber 203 is isolated from an anode chamber 201 by a cation exchange membrane 202.

An electrokinetic method for in-situ leaching of uranium used in this embodiment can break away from the simple principle of cone of depression, and an electric field is used to promote the pooling of uranium-carrying ions towards the pumping well 2, and the movement of colloids towards the injection well 1, and thus the probability of chemical clogging is reduced, and the migration of pollutants to the ambient environment is limited. The application of the electric field changes a migration mechanism of target ions from hydraulic-induced migration to electric field-triggered directional migration. Because the target element is obtained only through the dissolution and diffusion mechanism by simple pumping and injection, the ion diffusion rate is limited by the blocking effect of mineral particles, colloids and organic matters in the uranium ore, and the electrokinetic combined with in-situ pumping and injection is the applied electric field-fluid coupling diffusion and migration mechanism, thus the leaching efficiency is improved.

Figure 6:
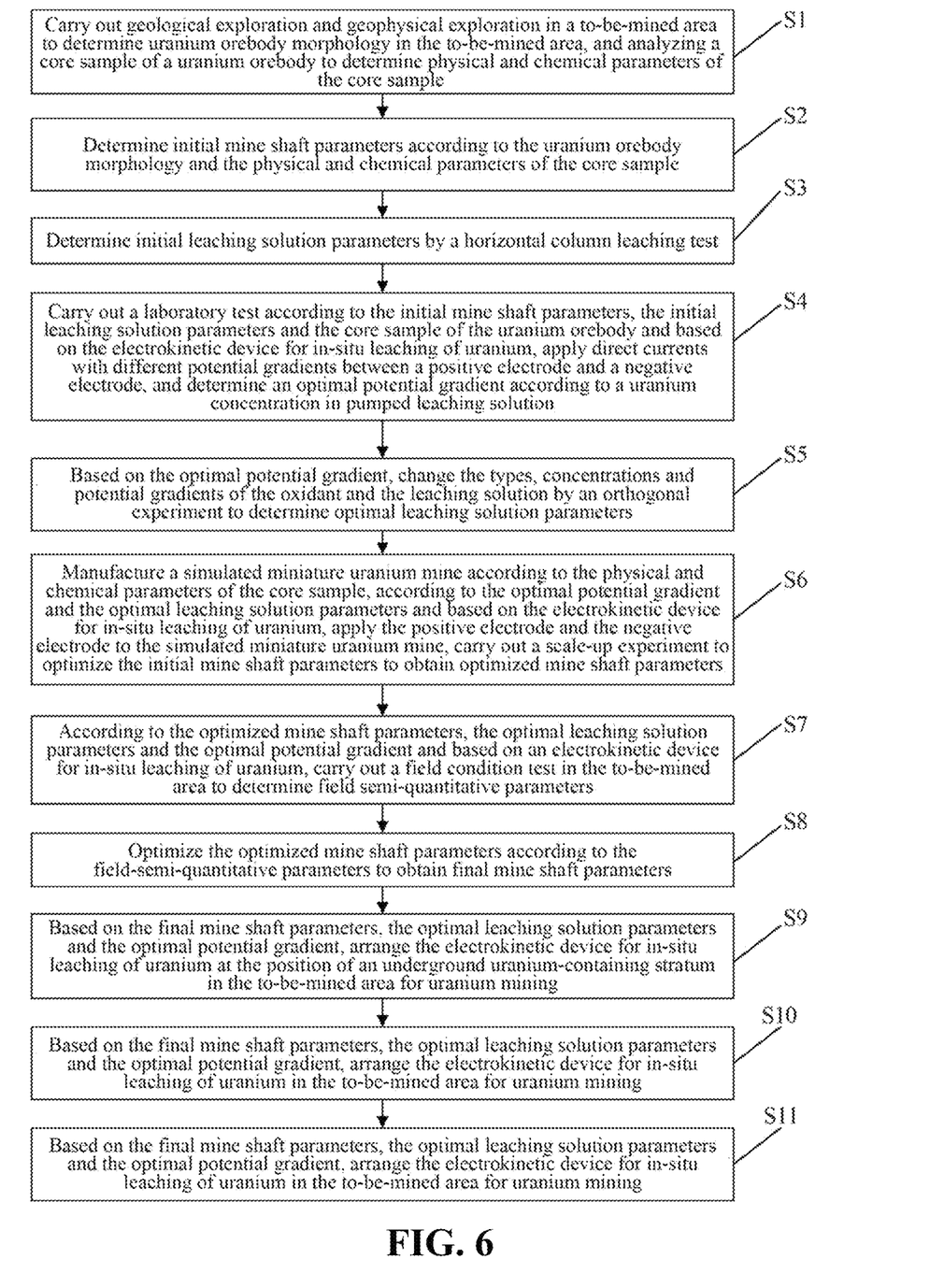
FIG. 6 is a flow chart of an electrokinetic method for in-situ leaching of uranium in accordance with the present disclosure.
Figure 7:
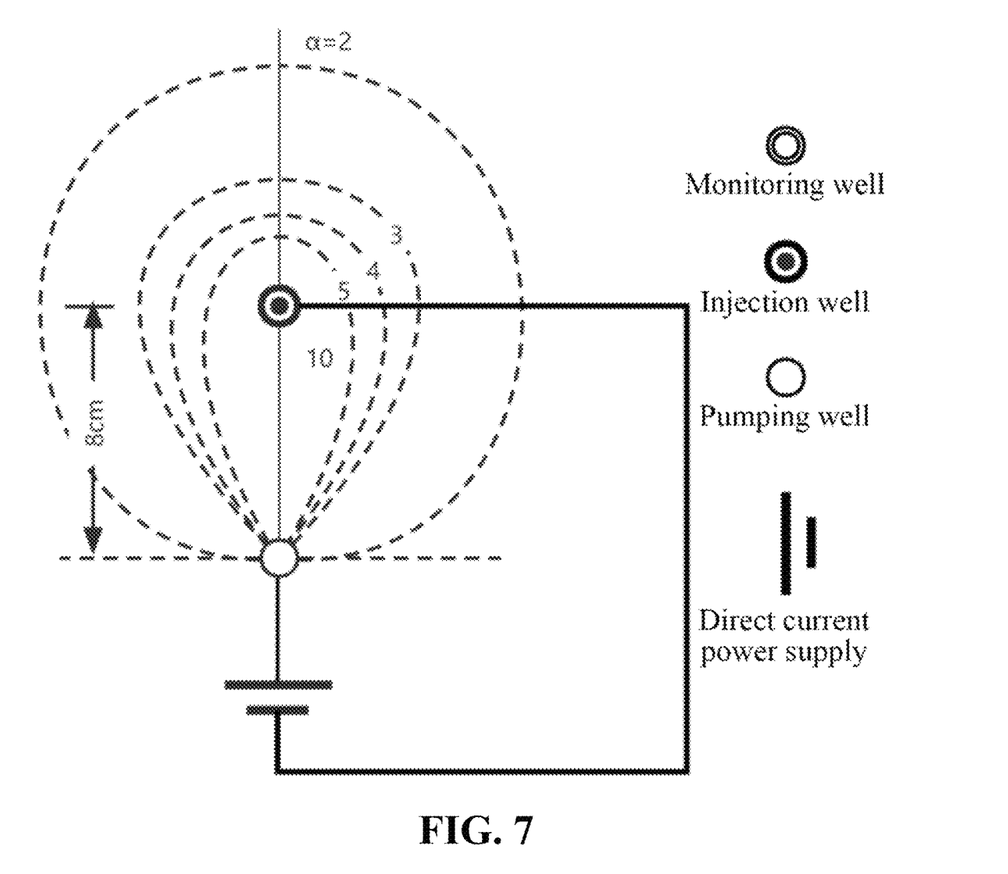
FIG. 7 is a structure schematic diagram of a two-spot well type.
Figure 8:
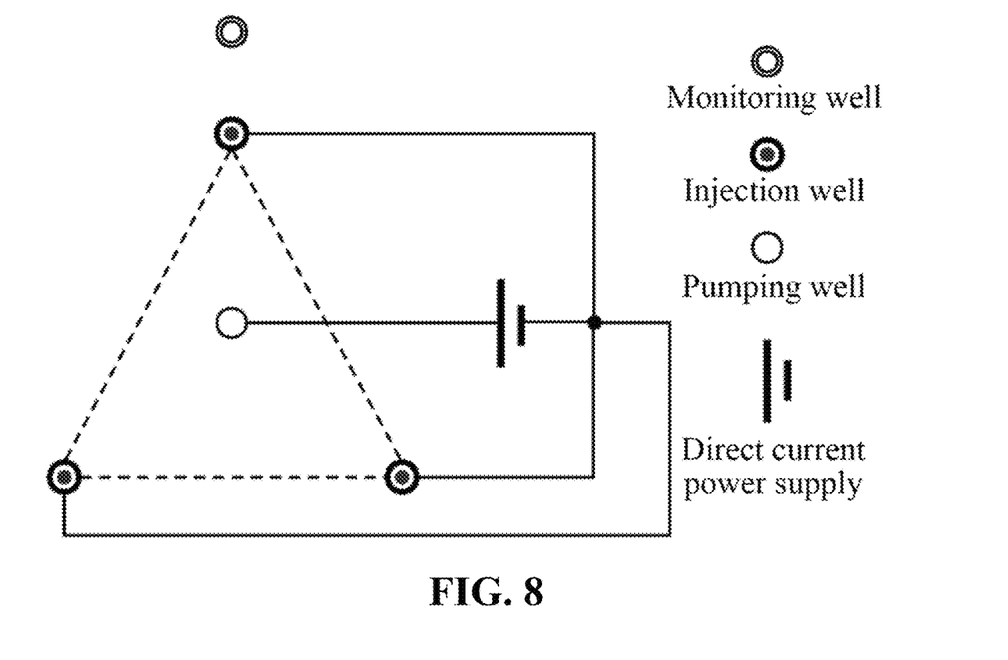
FIG. 8 is a structure schematic diagram of a four-spot well type.
Figure 9:
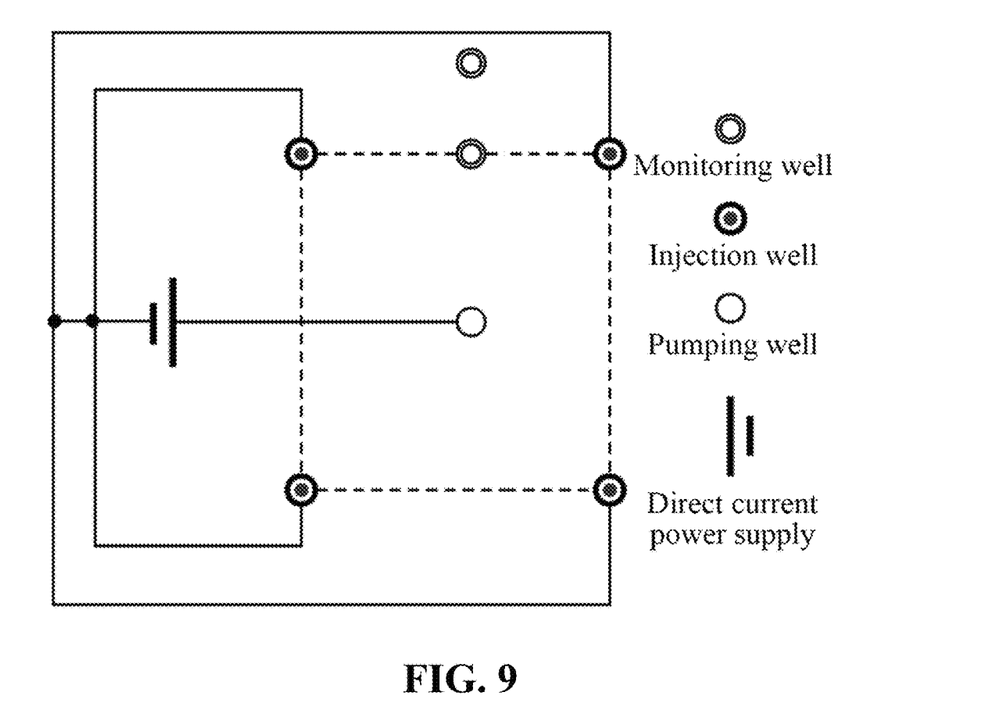
FIG. 9 is a structure schematic diagram of a five-spot well type.
Figure 10:
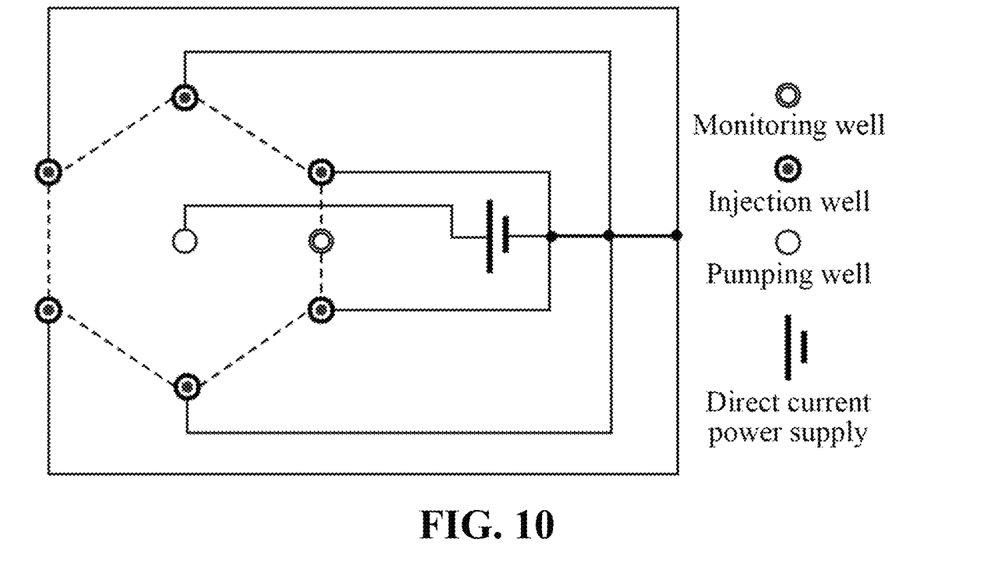
FIG. 10 is a structure schematic diagram of a seven-spot well type.

As shown in FIG. 6, an electrokinetic method for in-situ leaching of uranium includes the following steps:

S1: Geological exploration and geophysical exploration are carried out in a to-be-mined area to determine uranium orebody morphology in the to-be-mined area, and a core sample of a uranium orebody is analyzed to determine physical and chemical parameters of the core sample. Specifically, the drilled core sample of ore rock for electrokinetic in-situ leaching of uranium is subjected to TXRF, QXRD, mercury penetration/BET, SEM-EDS, CT scanning/nuclear magnetic resonance, FTIR, isotope, TOC, XPS and metagenome analysis as well as sequential extraction experiments, permeability and unit weight tests to determine the physical and chemical parameters of the core sample. The physical and chemical parameters of the core sample include uranium element composition, mineral composition, porosity, a pore structure, specific surface area, functional groups, major isotopes such as uranium oxysulfide, organic carbon, a chemical state, a molecular structure, microbial community composition, a mode of occurrence of uranium, a leaching dominant liquid-solid ratio, a permeability coefficient and unit weight.

S2: Initial mine shaft parameters are determined according to the uranium orebody morphology and the physical and chemical parameters of the core sample. The initial mine shaft parameters include well types, well diameters and well spacing of a pumping well and an injection well. Specifically, the basic well type is selected according to the orebody morphology, pore characteristics, permeability, a liquid-solid ratio, a pumping-injection ratio and other parameters, and a pumping-injection well pattern is arranged in an area for electrokinetic in-situ leaching of uranium. Combined with the buried depth of the orebody, ore permeability, ore grade, uranium amount per square meter, mineral composition and chemical composition of the ore, a leaching rate, a pumping-injection ratio and acid consumption, the well diameter and well spacing are initially set to be 15 m to 20 m in combination with economic indicators, a small value is taken when the porosity is low and the permeability is poor, otherwise, a large value is taken when the porosity is high and the permeability is excellent. An inner diameter of a pumping hole is set to be 128 mm to 395 mm, and a diameter of an injection hole is set to be 80 mm to 169 mm. The initial mine shaft parameters are determined by numerical simulation.

S3: Initial leaching solution parameters are determined by using a horizontal column leaching test. The initial leaching solution parameters include types, concentrations and solid-liquid ratios of an oxidant and a leaching agent. Specifically, technical parameters of the conventional in-situ leaching of uranium (initial leaching solution parameters) are determined by shaking flask experiments and conventional horizontal column leaching tests, e.g., types, concentrations and liquid-to-solid ratios of the oxidant (oxygen, hydrogen peroxide) and the leaching agent (sulfuric acid and $CO_2$ solution).

S4: According to the initial mine shaft parameters, the initial leaching solution parameters and the core sample of the uranium orebody, a laboratory test is carried out based on an electrokinetic device for in-situ leaching of uranium, direct currents with different potential gradients are applied between a positive electrode and a negative electrode, and an optimal potential gradient is determined according to a uranium concentration in pumped leaching solution. In this embodiment, electrode materials such as titanium oxide and graphite are used, and bar-like electrodes with a diameter of 20 mm to 72 mm are customized according to a thickness of an ore-bearing aquifer, which are respectively placed in a cathode chamber and an anode chamber and connected to casings.

Specifically, the core sample is used to carry out the horizontal column leaching test for electrokinetic in-situ leaching of uranium in a laboratory, specifically, the horizontal column leaching test device provided by above embodiment is used. Uranium ore in the electrokinetic device for in-situ leaching of uranium is the core sample of the uranium orebody. The potential gradients of 0 V/m, 20 V/m, 40 V/m, 60 V/m, 80 V/m and 100 V/m are selected and applied to the positive electrode and the negative electrode, respectively. The cathode chamber is connected to the negative electrode, and the anode chamber is connected to the positive electrode. Other parameters, such as the types, concentrations (including acid, alkali and neutral in-situ leaching) and dosage of the oxidant and leaching agent, are initially set to the same values as those of the conventional in-situ leaching of uranium. A uranium concentration, a current, a hydrogen ion concentration index, a pH value and a redox potential Eh value in the leaching solution are determined, and curves of the uranium concentration and a cumulative leaching rate changing with time are drawn, and the kinetic process and the optimal potential gradient of the electrokinetic in-situ leaching of uranium are preliminarily determined.

Above and below the optimal potential gradient, a series of voltages are selected according to the appropriate potential gradient for optimal analysis experiments, the uranium concentration and pH value in the leaching solution are determined, the curves of the uranium concentration and the cumulative leaching rate changing with time are drawn, and a phase diagram is drawn by simulation software to determine the optimal potential gradient and suitable pH range appropriate for studying electrokinetic in-situ leaching of uranium deposits.

S5: Based on the optimal potential gradient, the parameters, such as the types, concentrations and potential gradients, of the oxidant and the leaching solution are changed by an orthogonal experiment, so as to determine optimal leaching solution parameters. Specifically, on the basis of the optimal potential gradient, the orthogonal experiment method is used to change the parameters such as the types, concentrations and the potential gradients of the oxidants and the leaching agent, so as to determine the law of uranium leaching rate changing with time, establish a master equation, and construct a conceptual model and a mathematical model of electrokinetic in-situ leaching of uranium.

S6: A simulated miniature uranium mine is manufactured according to the physical and chemical parameters of the core sample, and according to the optimal potential gradient and the optimal leaching solution parameters and based on the electrokinetic device for in-situ leaching of uranium, the positive electrode and the negative electrode are applied to the simulated miniature uranium mine for a scale-up experiment, the initial mine shaft parameters are optimized to obtained optimized mine shaft parameters. Specifically, according to the physical and chemical parameters of the core sample, the simulated miniature uranium mine is manufactured by using an ore press, and the miniature uranium mine test device provided in the above embodiment is used to carry out the scale-up experiment of electrokinetic in-situ leaching of uranium, and the uranium ore in the miniature uranium mine test device is the simulated miniature uranium mine. The initial mine shaft parameters are verified and optimized by scale effect analysis, dimension analysis, heterogeneity analysis and conceptual model modification.

S7: According to the optimized mine shaft parameters, the optimal leaching solution parameters and the optimal potential gradient and based on the electrokinetic device for in-situ leaching of uranium, a field condition test is carried out on the to-be-mined area to determine field semi-quantitative parameters.

Specifically, a two-well method or a test unit composed of three or more injection wells, one pumping well, and two monitoring wells is used in the field to-be-mined area for field condition experiments, specifically as shown in FIG. 7 through FIG. 10: the total potential gradient remains unchanged, the negative electrode is connected to a cathode bar in the injection well (if three injection wells are used, the current is evenly divided into three clusters), and the positive electrode is connected to an anode bar in the pumping well, the oxidant, the leaching agent and the electrode protective solution are injected, and pumping and injection are carried out after electrifying, thus determining the semi-quantitative parameters of the electrokinetic in-situ leaching of uranium.

S8: The optimized mine shaft parameters are optimized according to the field semi-quantitative parameters to obtain final mine shaft parameters. Specifically, the feasibility of an industrial test is evaluated according to the field semi-quantitative parameters, and the mine shaft parameters are corrected and optimized in combination with a field flow field, seam heterogeneity and load capacity of mathematical calculation, and the final mine shaft parameters during the electrokinetic in-situ leaching of uranium are obtained.

Figure 11:
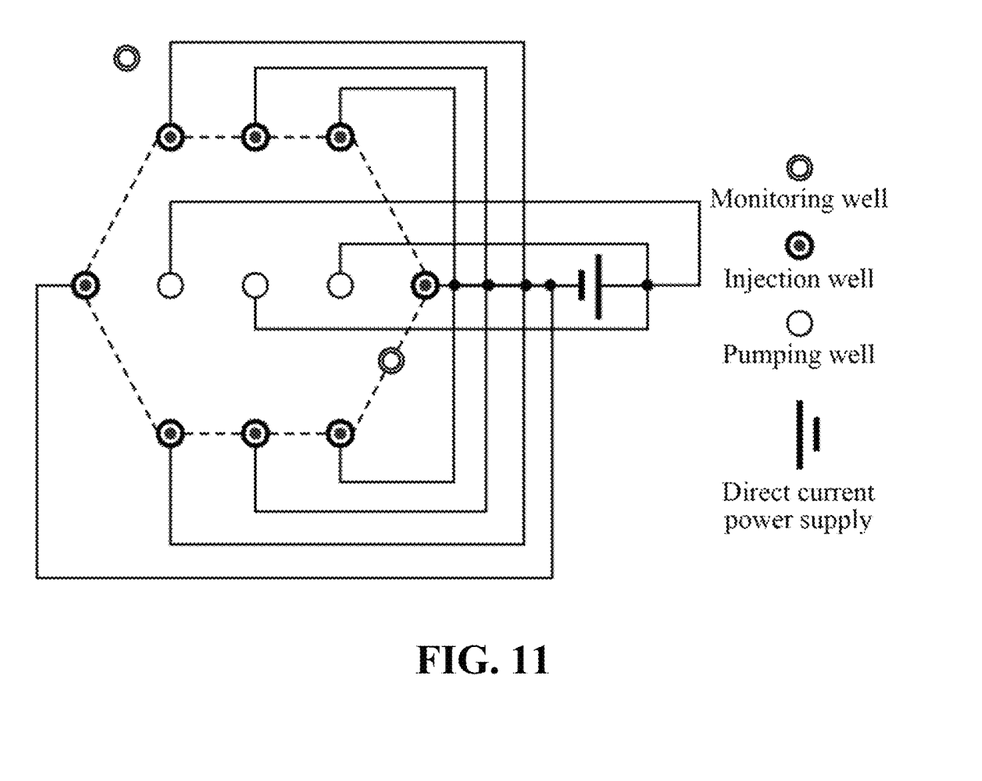
FIG. 11 is a structure schematic diagram of a leaching unit composed of three rows of boreholes.

S9: Based on the final mine shaft parameters, the optimal leaching solution parameters and the optimal potential gradient, the electrokinetic device for in-situ leaching of uranium is arranged at an underground uranium-containing stratum in the to-be-mined area for uranium mining. Specifically, after the field condition test is completed, a semi-industrial test for the electrokinetic in-situ leaching of uranium is carried out on a pre-mining uranium mine. The layout scheme of the well site is similar to that in the mining scheme, and is composed of three pumping wells, eight injection wells and one monitoring well. As shown in FIG. 11, the error between the semi-industrial test and large-scale production is reduced, and the method and process parameters are further optimized. At the periphery of the boundary of the area for electrokinetic in-situ leaching of uranium, one monitoring well is arranged every 100 m within the range of 1,000 m in an original groundwater flow direction, and the monitoring wells in other directions are provided according to the specific situation.

Further, the electrokinetic method for in-situ leaching of uranium further includes the following steps:

S10: A water sample in a uranium-containing stratum in the to-be-mined area is collected in real time and analyzed, so as to determine water sample. Specifically, the water sample is sampled from an ore-bearing aquifer for electrokinetic in-situ leaching of uranium, and is subjected to AAS, ICP-OES, ICP-MS, FTIR, pH, Eh, metagenome and isotope analysis for the determination of the water sample parameters. The water sample parameters include the content of background ions and organic functional groups in groundwater, levels of pH and Eh, microbial community composition, and size and distribution of major isotopes such as oxygen, sulfur and uranium.

S11: The influence of the uranium mining process on the ambient environment is determined according to the physical and chemical parameters of the core sample and the water sample parameters.

Specifically, prior to, during and after production, the core sample and the water sample are respectively tested and analyzed to determine the influence during the electrokinetic in-situ leaching of uranium on the ambient environment.

According to the present disclosure, the electrokinetic principle is applied to the in-situ leaching of uranium to construct a new method for in-situ leaching of uranium, i.e., a method of electrokinetic in-situ leaching of uranium (EK-ISLU). The feasibility, economy and key technological parameters of the method of electrokinetic in-situ leaching for uranium can be gradually determined through indoor thumbnail model tests, the miniature uranium mine device scale-up experiments, the field condition tests and the semi-industrial tests, and thus the uniformity of the leaching solution during transportation can be improved, the channeling phenomenon can be reduced, the leaching efficiency of the conventional permeable sandstone is increased, the permeability and porosity of low-permeability uranium ore are remarkably improved, and the grade of recoverable uranium resources is reduced.

It should be noted that the application of electric field during the acid, alkali and neutral in-situ leaching of uranium belongs to the scope of protection of the present disclosure.

Compared with the prior art, the present disclosure is wide in applicability, high in efficiency, economic and environment-friendly. The EK-ISLU technology provided by the present disclosure can reduce the economic mining grade of in-situ leaching of uranium ore samples to 0.01%, make the permeability as low as 0.1 m/d, increase the permeability of the uranium ore by 10% to 30%, increase the porosity by two orders of magnitude, and significantly improve the leaching efficiency.

Various embodiments in this specification are described in a progressive way, each embodiment focuses on the differences from other embodiments, and the same and similar parts between the various embodiments can be referred to each other. For the system disclosed in the embodiments, since the system corresponds to the method disclosed by the embodiments, the description thereof is relatively simple, and relevant matters references may be made to the description of the method.

Finally, it should be noted that the above embodiments are only used to illustrate the technical solutions of the present disclosure rather than limiting the same. Although the present disclosure has been described in detail with reference to the foregoing embodiments, it should be understood by those of ordinary skill in the art that it is still possible to modify the technical solutions recorded in the foregoing embodiments, or to equivalently replace some or all of technical features; and that these modifications or replacements do not make the essence of the corresponding technical solutions deviate from the scope of the technical solutions of the embodiments of the present disclosure.

What is claimed is:

1. An electrokinetic device for in-situ leaching of uranium, comprising:
   an injection well, a pumping well, a positive electrode, a negative electrode, leaching solution, and a direct current power supply;
   uranium ore is provided between the injection well and the pumping well;
   the negative electrode is arranged in the injection well;
   the positive electrode is arranged in the pumping well;
   the leaching solution is injected from the injection well, flows through the uranium ore, and then is pumped from the pumping well for uranium extraction;
   the direct current power supply is respectively connected to the positive electrode and the negative electrode, and is configured to apply direct current between the positive electrode and the negative electrode to promote pooling of uranium-carrying ions towards the pumping well;
   the injection well comprises a cathode chamber, an injection chamber, and an anion exchange membrane; the pumping well comprises an anode chamber, a pumping chamber, and a cation exchange membrane;

the anion exchange membrane is provided between the cathode chamber and the injection chamber, and the cation exchange membrane is provided between the anode chamber and the pumping chamber;

the negative electrode is arranged in the cathode chamber, and the positive electrode is arranged in the anode chamber;

the uranium ore is provided between the injection chamber and the pumping chamber; and the leaching solution is injected from the injection chamber, flows through the uranium ore, and then is pumped from the pumping chamber;

wherein the cathode chamber and the anode chamber each are filled with electrode protection solution.

2. The electrokinetic device for in-situ leaching of uranium according to claim 1, wherein the positive electrode and the negative electrode are both electrode bars.

3. The electrokinetic device for in-situ leaching of uranium according to claim 1, further comprising:

a first connector, respectively connected to the positive electrode and the cation exchange membrane and configured to fix the positive electrode to the cation exchange membrane; and a second connector, respectively connected to the negative electrode and the anion exchange membrane and configured to fix the negative electrode to the anion exchange membrane.

4. The electrokinetic device for in-situ leaching of uranium according to claim 1, further comprising:

a first filter, arranged in the injection well and attached to a well wall of the injection well; and a second filter, arranged in the pumping well and attached to a well wall of the pumping well.

5. The electrokinetic device for in-situ leaching of uranium according to claim 1, further comprising:

a first voltage-current monitoring component, arranged in the injection well and configured to detect a voltage and current in the injection well; and a second voltage-current monitoring component, arranged in the pumping well and configured to detect a voltage and current in the pumping well.

6. The electrokinetic device for in-situ leaching of uranium according to claim 1, wherein the injection well and the pumping well are both located in an underground uranium-containing stratum;

the electrokinetic device for in-situ leaching of uranium further comprises:

a first casing, extending from the ground to a top surface of the injection well; and a second casing, extending from the ground to a top surface of the pumping well.

* * * * *